(12) United States Patent
Moir et al.

(10) Patent No.: US 6,177,421 B1
(45) Date of Patent: Jan. 23, 2001

(54) AMOXICILLIN AND CLAVULANATE COMPOSITION

(75) Inventors: Peter Moir; Siobhan Greene, both of Clonmel (IE)

(73) Assignee: Fuisz International Ltd., Chantilly, VA (US)

( * ) Notice: Under 35 U.S.C. 154(b), the term of this patent shall be extended for 0 days.

(21) Appl. No.: 09/304,786

(22) Filed: May 4, 1999

(51) Int. Cl.⁷ .................. A61K 31/43; A61K 31/397
(52) U.S. Cl. ............................ 514/197; 514/210
(58) Field of Search ................... 514/197, 210

(56) References Cited

U.S. PATENT DOCUMENTS

| | | | |
|---|---|---|---|
| 4,301,149 | 11/1981 | Crowley | 424/114 |
| 4,441,609 | 4/1984 | Crowley | 206/204 |
| 4,537,887 | 8/1985 | Rooke et al. | 514/197 |
| 4,999,200 | * 3/1991 | Casilan | 424/480 |

FOREIGN PATENT DOCUMENTS

| | | |
|---|---|---|
| 2067900 | * 8/1981 | (GB) . |
| WO 92/19227 | 11/1992 | (WO) . |
| WO 94/16696 | 8/1994 | (WO) . |
| WO 96/34605 | 11/1996 | (WO) . |
| 97/33564 | * 9/1997 | (WO) . |

* cited by examiner

Primary Examiner—Phyllis G. Spivack
(74) Attorney, Agent, or Firm—John F. Levis; Richard D. Schmidt

(57) ABSTRACT

A storage-stable combination of at least one β-lactam antibiotic and at least one β-lactam inhibitor compressed into tablet form having a hardness of greater than 30 KP is disclosed.

17 Claims, No Drawings

AMOXICILLIN AND CLAVULANATE COMPOSITION

FIELD OF THE INVENTION

The present invention relates to compositions containing antibiotics and β-lactam inhibitors, and more particularly, to improved tablet formulations of amoxicillin and clavulanate having a low moisture content and excellent dissolution rates and bioavailabilities. The invention also relates to a novel method for making same.

BACKGROUND OF THE INVENTION

β-lactames are enzymes which open the β-lactam ring of such antibiotics as penicillins and cephalosporins to yield products which are devoid of antibacterial activity. Clavulanic acid or 3-(β-hydroxyethylidene)-7-oxo-4-oxa-1-azabicyclo [3,2,0]heptane-2-carboxylic acid, including its pharmaceutically acceptable salts and esters, has now been well-recognized as a medium potency antibiotic which inhibits the production of β-lactam enzymes, thereby enhancing the efficacy of β-lactam antibiotics.

In particular, the combination of clavulanic acid and amoxycillin has been shown to be particularly effective against β-lactams. The latter antibiotic is usually combined in a relatively large weight excess with the clavulanic acid to yield various pharmaceutical compositions. Dry, unit-dose compressed tablets for oral administration are just one example.

Unfortunately, in the preparation of many of these compositions the art has necessitated the inclusion of a complex formulation of excipients, including binders, glidants, disintegrants and even desiccants, etc. to yield a pharmaceutically acceptable carrier. This is in part due to the fact that clavulanate is a highly hygroscopic material which is highly unstable in aqueous media. Methods of formulation must therefore ensure that the product can retain its potency during storage, and yet can subsequently yield satisfactory dissolution rates. One such process is disclosed in WO 92/19227 and mandates the inclusion of both an intra-cellular and an extra-cellular disintegrant. Another process which is described in U.S. Pat. No. 4,537,887 specifies the inclusion of an edible desiccant within the composition itself. Other processes warrant the inclusion of a desiccant within a container housing the amoxycillin/clavulanate combination. In this regard, U.S. Pat. Nos. 4,301,149 and 4,441,609 are particularly salient.

What is therefore needed in the art is an improved tablet composition containing a β-lactam antibiotic such as amoxicillin and a β-lactamase inhibitor such as clavulanic acid which is simpler to manufacture and is highly moisture-resistant, and yet still presents a potent combination against β-lactames.

SUMMARY OF THE INVENTION

These and other objects of the invention are provided by a dry, unit-dose pharmaceutical composition comprising at least one β-lactam antibiotic in combination with at least one β-lactamase inhibitor, together with a pharmaceutically acceptable carrier. The composition contains one or more intra-cellular disintegrants, but does not comprise an extra-granular disintegrant. The composition is compressed to a hardness level which helps to ensure storage stability and moisture resistance, but which does not negatively affect dissolution/disintegration rates.

Further included as part of the invention is a method of forming a dry, unit-dose composition in tablet form containing at least one β-lactam antibiotic together with at least one pharmaceutically acceptable form of at least one β-lactamase inhibitor. The composition is prepared using intra-granular disintegrants, but without an extra-granular disintegrant. As part of the method, the composition is compressed to an acceptable hardness. By further incorporating a satisfactory level of intra-granular disintegrants, dissolution rates for the composition are good.

DETAILED DESCRIPTION OF THE PREFERRED EMBODIMENTS

It has now been discovered that a low moisture tablet formulation of antibiotic and β-lactam inhibitor may be prepared by compressing a mixture of the two active components.

The novel composition of the invention contains as one active component at least one β-lactam antibiotic. The antibiotic is selected from the group consisting of penicillins and cephalosporins and their pharmaceutically acceptable compounds, including the salts, esters, aldehydes and ketone products thereof, as well as mixtures of any of the foregoing. Preferred is the penicillin known in the art as amoxycillin in a pharmaceutically acceptable form. Especially desirable is amoxycillin. Even more preferred are the salts and esters of amoxycillin, including amoxicillin trihydrate.

A second active component of the invention is at least one β-lactamase inhibitor. Of these, clavulanic acid or one of its pharmaceutically acceptable compounds such as the salts or esters thereof are preferred. Potassium clavulanate (C6H8NO5K) is an especially preferred compound as the active component in the final formulation.

Any effective weight composition of the foregoing antibiotic(s) and β-lactam inhibitor(s) is desirable. An especially synergistic combination, however, will typically comprise an excess of antibiotic. Thus, a weight ratio of antibiotic to inhibitor will typically be within the range of about 10:1 to 1:1, more preferably about 6:1 to 1:1, and even more desirably about 3:1 to 1:1, with respect to the free forms of the respective compounds. In one particularly preferred embodiment, there will be about 2 parts of antibiotic for every 1 part of β-lactam inhibitor. Another particularly preferred embodiment will have about 4 parts antibiotic for every 1 part of inhibitor. Together, the antibiotic and inhibitor will comprise about 10 to 99.9% by weight of the final formulation, desirably about 20 to 80%, and more preferably will be within the range of about 30% to 45% thereof. On an actual weight basis, the composition will typically contain about 100 to 2000 milligrams of antibiotic with about 50 to 1000 milligrams of inhibitor, with respect to the free forms of the respective compounds. More preferably, there will be about 100 to 500 mg. of antibiotic for every 50 to 250 mg. of inhibitor. An especially preferred formulation of the composition of the invention will contain about 250 milligrams of antibiotic and about 125 grams of inhibitor. Another especially preferred formulation will have about 500 milligrams of antibiotic together with about 125 grams of β-lactam inhibitor. The foregoing weight amounts will vary, of course, depending upon the particular dosage loading desired by the skilled artisan.

The active components heretofore described are formulated with a pharmaceutically acceptable carrier. The carrier may be formed from pharmaceutical additives known in the art, and can include for example one or more of the following: disintegrants, glidants, adsorbents, lubricants, binders, fillers, and the like. Examples of suitable disintegrants include starches, sodium starch glycolate, croscarmellose sodium, formaldehyde, cross-linked N-vinyl-2-pyrrolidone (CLPVP), as well as various cellulosic compounds and materials known in the art. Of the foregoing, CLPVP and croscarmellose sodium are particularly useful, especially in combination. These are most preferably included in the formulation before compressing into a tablet or other final form, and hence may be referred to as "intra-granular" disintegrants. It is especially preferred that the final formulation not contain any extra-granular disintegrants. As that term is used herein, "extra-granular" refers to the intermediary product stage after the active ingredients have been blended together with any additives, pressed into slugs and milled into granulates, but before they have been pressed into dosage units such as tablets or otherwise shaped into a final dosage form. Disintegrant(s) will comprise at least about 4% of the final formulation (on a total weight basis), and more preferably will make up at least about 6% thereof. In certain embodiments, there will be at least about 8% of disintegrants or more in the composition.

Suitable lubricants include the long-chain fatty acids, such as stearic acid or salts thereof, and in particular the Group II metal salts of magnesium and calcium such as magnesium stearate. Silicon dioxide may be also be utilized for its glidant and adsorbent/anti-caking properties. The foregoing lubricant additive(s) together will comprise about 0 to 10% of the final formulation, and more desirably will be within the range of about 0.1 to 5% thereof, even more preferably about 1 to 5% thereof.

The filler material, e.g. microcrystalline cellulose, will typically comprise about 10 to 95% of the final formulation. In a preferred embodiment, the filler will make up about 55 to 75% of the final formulation. Filler material can include any inert pharmaceutical bulking agent or material. Preferably, microcrystalline cellulose is utilized, since it also possesses certain binding and disintegrating properties.

Also optionally included are one or more flavoring agents, coloring agents and preservatives in amounts of from about 0 to 5% of the final formulation. These may be selected from known compounds typically available to the skilled artisan.

Preferably, the final formulation is in tablet dosage form, but other forms such as capsules, granulates, sachets and powders are also envisioned.

To prepare the final composition of the invention in tablet form, the following procedure may be utilized: The active ingredients together with one or more additives are first blended, and then are pressed into slugs, milled and mixed with any remaining additives, and then pressed into tablets using standard presses. The tablets may be further coated with one or more pharmaceutical grade coating materials known in the industry. Typically, the coating adds about 1 to 10% by weight to the final formulation, preferably about 3–5%.

It is within the various embodiments herein set forth that the final tablet formulation be compressed to a hardness of at least about 15 kilopoise (Kp), and more preferably at least about 20 Kp. It is even more preferable that the final compressed tablets have a hardness of at least about 25 Kp or more. It is especially desirable that the hardness level be greater than about 30 Kp. The applicant has now discovered that by increasing tablet compression hardness, together with the addition of a certain level of intra-granular disintegrant(s) as heretofore described, the resultant tablet is highly resistant to the actions of moisture while at the same time maintaining excellent dissolution rates.

The moisture content of the final tablet formulation is very low. The various embodiments herein set forth will have a moisture content not exceeding about 10% (by weight). Even more desirably, the final moisture content will not exceed about 8%, and even more preferably will not be in excess of about 6% or even lower.

The compositions according to the various embodiments herein described are highly storage stable due to their relatively high compression rates and low moisture content.

EXAMPLES

The following examples illustrate various embodiments of the invention. These should not be construed as limiting the scope thereof however.

Examples 1 and 2

In Example 1, tablet formulations containing 250 mg. of amoxycillin and 125 mg. of clavulanate was prepared. In Example 2, tablets containing 500 mg. of amoxicillin and 125 mg. of clavulanate was formulated. The unit-dose formulations are set forth below in TABLE 1:

TABLE 1

| Formulation | Example 1 (250/125 mg) | Example 2 (500/125 mg) |
|---|---|---|
| Amoxicillin Trihydrate Compacted B.P. | X | X |
| Potassium Clavulanate/Avicel pH 112 (1:1) | XX | XX |
| Crospovidone E.P. | 30.0 mg. | 45.0 mg. |
| Amorphous Silicon Dioxide (Aerosil 200) E.P. | 6.0 mg. | 9.0 mg. |
| Magnesium Stearate E.P. | 13.3 mg. | 20.0 mg. |
| Croscarmellose Sodium (Ac-Di-Sol) E.P. | 26.7 mg. | 40.0 mg. |
| Microcrystalline Cellulose (Avicel pH 112) E.P. | XXX | XXX |
| Total Uncoated | 693 mg. | 1040 mg. |
| Total Coated | 721 mg. | 1082 mg. |

X = potency dependent
XX = potency dependent, and a ~5% overage is included on Clavulanic Acid
XXX = dependent on combined active potencies

Example 3

This example sets forth the process utilized in preparing the formulation of Examples 1 and 2. All materials were weighed. Aerosil 200 was sieved. A blender was loaded with amoxicillin trihydrate (compacted for direct compression use), sieved Aerosil, croscarmellose sodium, and a portion of crospovidone and mixed. The remaining crospovidone was added, along with Avicel pH 112. The potassium clavulanate/Avicel pH 112 (1:1) mixture was sieved into the blender. The total was mixed, and 0.5 kg. of magnesium stearate was added to the blender and blended. This blend was then precompressed into slugs. These slugs were then passed through the Stokesmill. The second fraction of the magnesium stearate was sieved into the blender and blended for 3 minutes. The blend was transferred to drums using silica gel between the bags. The yield limits were 95 to 100.5%. Tableting was carried out on a compression machine. The average weight was 693 mg. for the 2/1 combination and 1040 mg. for the 4/1 combination. Film coating was carried out using a sprayer. Tablets are coated until a weight increase of about 4% is recorded. Upon completion of coating the spraying was terminated and the tablets were tumbled dry for about 5 minutes, and discharged into tared drums with the yield recorded.

Examples 4 and 5

These examples provide various specifications for 3 batches each of the 375 mg. (2/1) and the 625 mg. (4/1)

formulations of co-amoxiclav coated tablets in Tables 2 and 3, respectively. Each of the batches was prepared in accordance with the data and procedures set forth in Examples 1 and 2 above:

TABLE 2

(375 mg.) (2/1)

| Test | Specification | Batch No. 1 | Batch No. 2 | Batch No. 3 |
|---|---|---|---|---|
| Disintegration | Max. 30 mins. | 11 mins. | 12 mins. | 12 mins. |
| Moisture | No More Than 7.5% | 7.28% | 6.21% | 5.43% |
| Dissolution: | | | | |
| Amoxicillin | 85% (Q) | 90% | 94% | 91% |
| Clavulanic Acid | 80% (Q) | 97% | 102% | 98% |
| Hardness | Min. 15 Kp | 31.3 Kp | 33.0 Kp | 26.5 Kp |

TABLE 3

(625 mg. 4/1)

| Test | Specification | Batch No. 1 | Batch No. 2 | Batch No. 3 |
|---|---|---|---|---|
| Disintegration | Max. 30 mins. | 10 mins. | 9 mins. | 11 mins. |
| Moisture | No More Than 10.5% | 8.3% | 9.0% | 8.7% |
| Dissolution: | | | | |
| Amoxicillin | 85% (Q) | 92% | 89% | 86% |
| Clavulanic Acid | 80% (Q) | 102% | 102% | 102% |
| Hardness | Min. 15 Kp | 33.6 Kp | 34.3 Kp | 34.9 Kp |

It is expected that certain changes or modifications to the invention herein described may be effected by those skilled in the art without departing from the true spirit and scope thereof as set forth in the claims and the accompanying specification.

What is claimed is:

1. A dry, unit-dose pharmaceutical composition comprising at least one β-lactam antibiotic in combination with at least one β-lactamase inhibitor, together with a pharmaceutically acceptable carrier, wherein said composition does not comprise an extra-granular disintegrant, said composition being compressed into a tablet having a hardness of greater than about 30 KP.

2. The composition of claim 1, wherein said antibiotic is at least one member selected from the group consisting of penicillins and cephalosporins and the pharmaceutically acceptable versions thereof, and said inhibitor comprises clavulanic acid, its pharmaceutical salts, esters, aldehydes and ketone products thereof.

3. The composition of claim 2, wherein said antibiotic is amoxycillin, its pharmaceutically acceptable salts and esters.

4. The composition of claim 3, wherein said amoxycillin is amoxicillin trihydrate and said inhibitor is potassium clavulanate.

5. The composition of claim 2, wherein said pharmaceutically acceptable carrier is at least one additive selected from the group consisting of disintegrants, glidants, adsorbents, lubricants, fillers, and binders.

6. The composition of claim 5, wherein said disintegrant is at least one member selected from the group consisting of N-vinyl-2-pyrrolidone and croscarmellose sodium.

7. The composition of claim 5, wherein said lubricant is at least one member selected from the group consisting of the Group II metallic salts of stearic acid.

8. The composition of claim 2, wherein said hardness is at least about 20 KP.

9. The composition of claim 2, said composition having a weight ratio of antibiotic to inhibitor within the range of from about 10:1 to 1:1.

10. The composition of claim 9, wherein said composition has a weight ratio within the range of about 5:1 to 1:1.

11. A method of forming a unit-dose pharmaceutical composition comprising the steps of:
    a) forming an admixture of amoxicillin and at least one derivative of clavulanic acid together with at least one intra-granular disintegrant;
    b) pressing the admixture obtained from step a) into a slug;
    c) milling said slug;
    d) tableting the mixture of step c) without the addition of extra-granular disintegrants into a unit dosage form to a hardness level of greater than about 25 KP.

12. The method of claim 11, wherein said disintegrant comprises at least about 4% of said composition.

13. The tablet prepared according to the method of claim 11.

14. A pharmaceutical composition comprising at least one β-lactam antibiotic, at least one β-lactamase inhibitor and at least one intra-granular disintegrant, said composition being prepared according to the process of:
    a) admixing said antibiotic, said inhibitor and said intra-granular disintegrant;
    b) pressing the admixture obtained from step a) into slugs;
    c) milling said slugs; and
    d) tabletting the mixture of step c) without the addition of extra-granular disintegrants into unit dosage forms having a hardness value of greater than about 30 KP.

15. The composition of claim 14, wherein said antibiotic is amoxicillin and said inhibitor is clavulanate.

16. The composition of claim 15, wherein said intra-granular disintegrant is at least one member selected from the group consisting of N-vinyl-2-pyrrolidone and croscarmellose sodium.

17. The composition of claim 16, wherein said intra-granular disintegrant is a combination of N-vinyl-2-pyrrolidone and croscarmellose sodium.

* * * * *